United States Patent [19]
Jørgensen et al.

[11] Patent Number: 6,060,468
[45] Date of Patent: May 9, 2000

[54] N-SUBSTITUTED AZAHETEROCYCLIC COMPOUNDS

[75] Inventors: Tine Krogh Jørgensen, Herlev; Erik Fischer, Charlottenlund; Rolf Hohlweg, Kvistgaard; Knud Erik Andersen, Smørum; Uffe Bang Olsen, Vallensbæk, all of Denmark; Zdenek Polivka, Praha, Czechoslovakia; Vladimir Valenta, Praha, Czechoslovakia; Karel Sindelár, Praha, Czechoslovakia

[73] Assignee: Novo Nordisk A/S, Bagsvaerd, Denmark

[21] Appl. No.: 08/943,368

[22] Filed: Oct. 3, 1997

[30] Foreign Application Priority Data

Oct. 4, 1996 [DK] Denmark .................. 1091/96

[51] Int. Cl.[7] .............. C07D 337/14; C07D 491/113; C07D 211/90; A61K 31/445
[52] U.S. Cl. ............. 514/218; 514/232.8; 514/255; 514/256; 514/275; 514/320; 514/324; 514/326; 514/337; 514/352; 514/365; 514/382; 514/396; 514/422; 514/431; 514/450; 540/553; 544/147; 544/145; 544/375; 544/297; 544/327; 544/326; 546/196; 546/202; 546/279.7; 546/281.7; 546/148; 546/165; 548/518; 548/311.4; 548/250; 548/132; 548/131; 548/202; 548/962; 548/525; 548/527; 549/12; 549/354; 549/59; 549/60
[58] Field of Search .................. 546/202, 196, 546/279.7, 281.7, 148, 165; 514/324, 218, 320, 326, 337, 232.8, 352, 365, 382, 255, 396, 422, 431, 450, 256, 275; 549/12, 354, 59, 60; 548/518, 311.4, 250, 132, 131, 202, 962, 525, 527; 544/147, 145, 375, 297, 326, 327; 540/553

[56] References Cited

FOREIGN PATENT DOCUMENTS

| | | |
|---|---|---|
| 268 628 | 7/1990 | Czechoslovakia . |
| 268 500 | 8/1990 | Czechoslovakia . |
| 268 626 | 8/1990 | Czechoslovakia . |
| 264 541 | 12/1990 | Czechoslovakia . |
| 0 321 100 A2 | 6/1989 | European Pat. Off. . |
| WO 96/31472 | 10/1996 | WIPO . |

OTHER PUBLICATIONS

Valenta et al., Collect. Czech. Chem. Commun., vol. 54, pp. 1403–1421, 1989.
Bártl et al., Collect. Czech. Chem. Commun., vol., 49, pp. 1810–1815, 1984.
Jílek et al., Collect. Czech. Chem. Commun., vol., 53, pp. 2731–2741, 1988.
Abstract—The Abstract No. 183364g, vol., 115, No. 17, p. 935, 1991.
Abstract—The Abstract No. 49722u, vol., 115, No. 5, p. 854, 1991.
Abstract—The Abstract No.57689a, vol. 110, No. 7, p. 696, 1989.
CAS printout of structures of CS 268626, Mar. 14, 1990.

*Primary Examiner*—Mukund J. Shah
*Assistant Examiner*—Bruck Kifle
*Attorney, Agent, or Firm*—Steve Zelson, Esq.; Elias Lambiris, Esq.

[57] ABSTRACT

The present invention relates to novel N-substituted azaheterocyclic compounds of the general formula

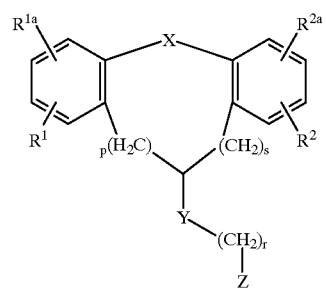

wherein X, Y, Z, $R^1$, $R^{1a}$, $R^2$, $R^{2a}$, p, r and s are as defined in the detailed part of the present description or salts thereof, to methods for their preparation, to compositions containing them, and to their use for the clinical treatment of painful, hyperalgesic and/or inflammatory conditions in which C-fibers play a pathophysiological role by eliciting neurogenic pain or inflammation as well as their use for treatment of indications caused by or related to secretion and circulation of insulin antagonising peptides.

33 Claims, No Drawings

N-SUBSTITUTED AZAHETEROCYCLIC COMPOUNDS

FIELD OF INVENTION

The present invention relates to novel N-substituted azaheterocyclic compounds in which a substituted alkyl chain forms part of the N-substituent or salts thereof, to methods for their preparation, to compositions containing them, to the use of the compounds for preparing compositions for the clinical treatment of painful, hyperalgesic and/or inflammatory conditions in which C-fibres play a pathophysiological role by eliciting neurogenic pain or inflammation, and to methods of treating said painful, hyperalgesic and/or inflammatory conditions. The invention also relates to the use of the present compounds for reducing blood glucose and/or inhibit the secretion, circulation or effect of insulin antagonising peptides like CGRP or amylin, the present compounds being known to interfere with neuropeptide containing C-fibres. Hence the present compounds can be used in the treatment of insulin resistance in non-insulin-dependent diabetes mellitus (NIDDM) in order to improve the glucose tolerance as well as ageing-associated obesity.

BACKGROUND OF INVENTION

The nervous system exerts a profound effect on the inflammatory response. Antidromic stimulation of sensory nerves results in localised vasodilation and increased vascular permeability (Janecso et al. Br. J. Pharmacol. 1967, 31, 138–151) and a similar response is observed following injection of peptides known to be present in sensory nerves. From this and other data it is postulated that peptides released from sensory nerve endings mediate many inflammatory responses in tissues like skin, joint, urinary tract, eye, meninges, gastrointestinal and respiratory tracts. Hence inhibition of sensory nerve peptide release and/or activity, may be useful in treatment of, for example arthritis, dermatitis, rhinitis, asthma, cystitis, gingivitis, thrombophlelitis, glaucoma, gastrointestinal diseases or migraine.

Further, the potent effects of CGRP on skeletal muscle glycogen synthase activity and muscle glucose metabolism, together with the notion that this peptide is released from the neuromuscular junction by nerve excitation, suggest that CGRP may play a physiological role in skeletal muscle glucose metabolism by directing the phosphorylated glucose away from glycogen storage and into the glycolytic and oxidative pathways (Rossetti et al. Am. J. Physiol. 264, E1–E10, 1993). This peptide may represent an important physiological modulator of intracellular glucose trafficking in physiological conditions, such as exercise, and may also contribute to the decreased insulin action and skeletal muscle glycogen synthase in pathophysiological conditions like NIDDM or ageing-associated obesity (Melnyk et al. Obesity Res. 3, 337–344, 1995) where circulating plasma levels of CGRP are markedly increased. Hence inhibition of release and/or activity of the neuropeptide CGRP may be useful in the treatment of insulin resistance related to type 2 diabetes or ageing.

In U.S. Pat. Nos. 4,383,999 and 4,514,414 and in EP 236342 as well as in EP 231996 some derivatives of N-(4,4-disubstituted-3-butenyl)azaheterocyclic carboxylic acids are claimed as inhibitors of GABA uptake. In EP 342635 and EP 374801, N-substituted azaheterocyclic carboxylic acids in which an oxime ether group and vinyl ether group forms part of the N-substituent respectively are claimed as inhibitors of GABA uptake. Further, in WO 9107389 and WO 9220658, N-substituted azacyclic carboxylic acids are claimed as GABA uptake inhibitors. EP 221572 claims that 1-aryloxyalkylpyridine-3-carboxylic acids are inhibitors of GABA uptake.

WO 9631472, WO 9631473 and WO 9631483, all of which are published on Oct. 10 1996 discloses N-substituted azaheterocyclic compounds.

SUMMARY OF THE INVENTION

The present invention relates to compounds of the general formula I, wherein X, Y, Z, $M_1$, $M_2$, $R^1$ through $R^{20}$, p, q, r, s, n, m and u are as defined in the detailed part of the present description.

The present compounds are useful for the treatment, prevention, elimination, alleviation or amelioration of an indication related to all painful, hyperalgesic and/or inflammatory conditions in which C-fibres play a pathophysiological role, e.g. neurogenic pain, inflammation, migraine, neuropathy, itching and rheumatoid arthritis, as well as indications caused by or related to the secretion and circulation of insulin antagonising peptides, e.g. non-insulin-dependent diabetes mellitus (NIDDM) and ageing-associated obesity.

In another aspect, the present invention includes within its scope pharmaceutical compositions comprising, as an active ingredient, at least one of the compounds of the general formula I or a pharmaceutically acceptable salt thereof together with a pharmaceutically acceptable carrier or diluent.

In another aspect of the present invention there is provided a method of treating painful, hyperalgesic and/or inflammatory conditions in which C-fibres play a pathophysiological role, e.g. neurogenic pain, inflammation, migraine, neuropathy, itching and rheumatoid arthritis, as well as a method of treating indications caused by or related to the secretion and circulation of insulin antagonising peptides like CGRP or amylin, e.g. non-insulin-dependent diabetes mellitus (NIDDM) and ageing-associated obesity. The method of treating may be described as the treatment of one of the above indications in a subject in need thereof, which comprises the step of administering to the said subject a neurologically effective amount of a compound of the invention, or a pharmaceutically acceptable salt thereof.

A further aspect of the invention relates to the use of a compound of the present invention for the preparation of a pharmaceutical composition for the treatment of all painful, hyperalgesic and/or inflammatory conditions in which C-fibres play a pathophysiological role, e.g. neurogenic pain, inflammation, migraine, neuropathy, itching and rheumatoid arthritis, as well as for the treatment of indications caused by or related to the secretion and circulation of insulin antagonising peptides, e.g. non-insulin-dependent diabetes mellitus (NIDDM) and ageing-associated obesity.

Further objects will become apparent from the following description.

DETAILED DESCRIPTION OF THE INVENTION

Accordingly, the present invention relates to novel N-substituted azaheterocyclic compounds of formula I

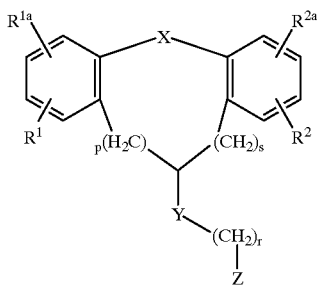

(I)

wherein $R^1$, $R^{1a}$, $R^2$ and $R^{2a}$ independently are hydrogen, halogen, trifluoromethyl, hydroxy, $C_{1-6}$-alkyl, $C_{1-6}$-alkoxy or methylthio, —$NR^7R^8$ or —$SO_2NR^7R^8$ wherein $R^7$ and $R^8$ independently are hydrogen or $C_{1-6}$-alkyl; and X is completion of an optional bond, ortho-phenylene, —O—, —S—, —$C(R^9R^{10})$—, —(C=O)—, —$N(R^3)$—, —(S=O)—, —$CH_2$—(C=O)—, —(C=O)—$CH_2$—, —$N(R^4)$—(C=O)—, —(C=O)—$N(R^4)$—, —O—$CH_2$—, —$CH_2$—O—, —S—$CH_2$—, —$CH_2$—S—, —$CH_2CH_2$—, —CH=CH—, —O—$CH_2$—O—, —$(CH_2)N(R^3)$—, —$N(R^3)(CH_2)$—, —$N(CH_3)SO_2$—, —$SO_2N(CH_3)$—, —$CH(R^{10})CH_2$—, —$CH_2CH(R^{10})$—, —CH=CH—$CH_2$—, —$CH_2$—CH=CH—, —$CH_2CH_2CH_2$— or —$CH_2$—O—$CH_2$— wherein $R^9$ is hydrogen or $C_{1-6}$-alkyl, and $R^{10}$ is $C_{1-6}$-alkyl or phenyl optionally substituted with halogen, trifluoromethyl, hydroxy, $C_{1-6}$-alkyl or $C_{1-6}$-alkoxy, and $R^4$ and $R^3$ independently are hydrogen, $C_{1-6}$-alkyl or phenyl optionally substituted with halogen, trifluoromethyl, hydroxy, $C_{1-6}$-alkyl or $C_{1-6}$-alkoxy; and Y is —O—, —$S(O)_q$— wherein q is 0, 1 or 2, or —$N(R^5)$— wherein $R^5$ is hydrogen or $C_{1-6}$-alkyl; and s is 0 or 1 and p is 0 or 1 provided that s or p must not be 0 at the same time; and r is 1, 2, 3 or 4; and Z is selected from

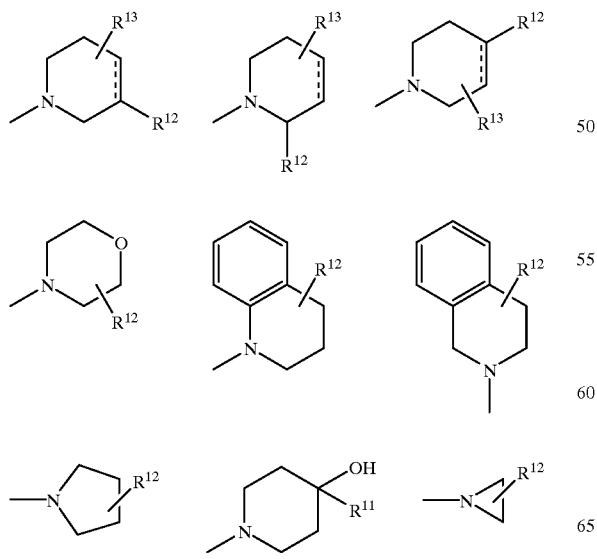

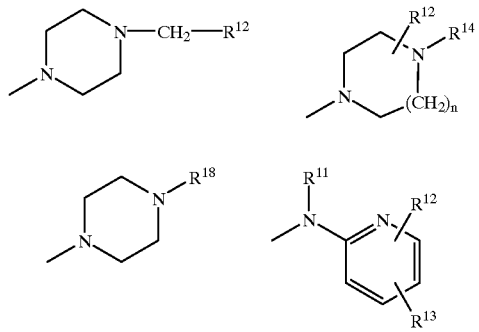

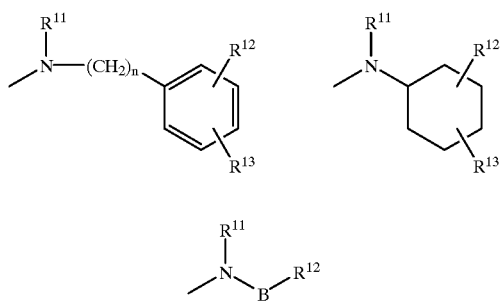

wherein n is 0, 1 or 2; and $R^{11}$ is hydrogen, $C_{1-6}$-alkyl, $C_{1-6}$-alkoxy or phenyl optionally substituted with halogen, triflouromethyl, hydroxy, $C_{1-6}$-alkyl or $C_{1-6}$-alkoxy; and $R^{12}$ is —$(CH_2)_mOH$ or —$(CH_2)_uCOR^{17}$ wherein m is 0, 1, 2, 3, 4, 5 or 6 and u is 0 or 1;

and wherein $R^{17}$ is —OH, —$NHR^{20}$ or $C_{16}$-alkoxy, wherein $R^{20}$ is hydrogen or $C_{1-6}$-alkyl; and $R^{13}$ is hydrogen, halogen, trifluoromethyl, hydroxy, $C_{1-6}$-alkyl or $C_{1-6}$-alkoxy; and $R^{14}$ is hydrogen or $C_{1-6}$-alkyl; and B is $C_{1-6}$-alkylene, $C_{2-6}$-alkenylene or $C_{2-6}$-alkynylene; and is optionally a single bond or a double bond; and $R^{18}$ is selected from

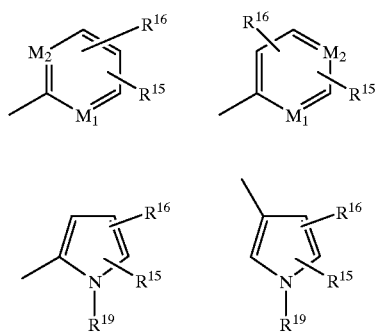

wherein $M_1$ and $M_2$ independently are C or N; and $R^{19}$ is hydrogen, $C_{1-6}$-alkyl, phenyl or benzyl; and $R^{15}$ is hydrogen, halogen, trifluoromethyl, nitro or cyano;

and $R^{16}$ is hydrogen, halogen, trifluoromethyl, nitro, cyano, —$(CH_2)_mCOR^{17}$, —$(CH_2)_mOH$ or —$(CH_2)_mSO_2R^{17}$, wherein m is 0, 1 or 2;
or $R^{16}$ is selected from

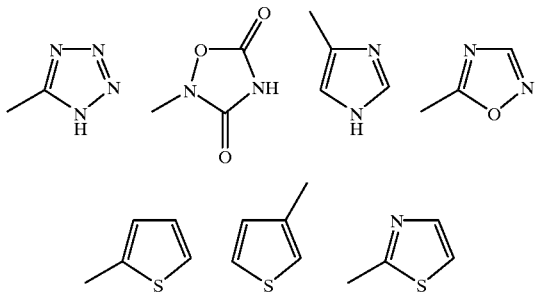

or a pharmaceutically acceptable salt thereof.

Compounds of formula I wherein X is completion of an optional bond, —$C(R^9R^{10})$—, —(C=O)—, —$N(R^3)$—, —$CH_2$—(C=O)—, —(C=O)—$CH_2$—, —$N(R^4)$—(C=O)—, —(C=O)—$N(R^4)$—, —O—$CH_2$—, —$CH_2$—O—, —S—$CH_2$—, —$CH_2$—S—, —$(CH_2)N(R^3)$—, —$N(R^3)(CH_2)$—, —$N(CH_3)SO_2$—, —$SO_2N(CH_3)$—, —$CH(R^{10})CH_2$—, —$CH_2CH(R^{10})$—, —CH=CH—$CH_2$—, —$CH_2$—CH=CH— or —$CH_2CH_2CH_2$— wherein $R^9$ is hydrogen or $C_{1-6}$-alkyl, and $R^{10}$ is $C_{1-6}$-alkyl or phenyl optionally substituted with halogen, trifluoromethyl, hydroxy, $C_{1-6}$-alkyl or $C_{1-6}$-alkoxy, and $R^4$ and $R^3$ independently are hydrogen or $C_{1-6}$-alkyl, and wherein $R^1$, $R^2$, Y, s, p, r and Z are as described above, are known from WO 9631472, WO 9631473 and WO 9631483.

The compounds of formula I may exist as geometric and optical isomers and all isomers, as separated, pure or partially purified stereoisomers or racemic mixtures thereof are included in the scope of the invention. Isomers may be separated by means of standard methods such as chromatographic techniques or fractional crystallisation of suitable salts.

Preferably, the compounds of formula I exist as the individual geometric or optical isomers.

The compounds according to the invention may optionally exist as pharmaceutically acceptable acid addition salts or—when the carboxylic acid group is not esterified—as pharmaceutically acceptable metal salts or—optionally alkylated—ammonium salts.

Examples of such salts include inorganic and organic acid addition salts such as hydrochloride, hydrobromide, sulphate, phosphate, acetate, fumarate, maleate, citrate, lactate, tartrate, oxalate or similar pharmaceutically acceptable inorganic or organic acid addition salts, and include the pharmaceutically acceptable salts listed in Journal of Pharmaceutical Science, 66, 2 (1977) which are known to the skilled artisan.

Also included are the hydrates of the above mentioned acid addition salts which the present compounds are able to form.

The acid addition salts may be obtained as the direct products of compound synthesis. In the alternative, the free base may be dissolved in a suitable solvent containing the appropriate acid, and the salt isolated by evaporating the solvent or by precipitation or crystallisation.

The compounds of formula I may be administered in a pharmaceutically acceptable acid addition salt form or where possible as a metal or a lower alkylammonium salt. Such salt forms exhibit approximately the same order of activity as the free base forms.

In the above structural formula and throughout the present specification, the following terms have the indicated meaning:

The term "$C_{1-6}$-alkyl" as used herein, alone or in combination, refers to a straight or branched, saturated hydrocarbon chain having 1 to 6 carbon atoms such as e.g. methyl, ethyl, n-propyl, isopropyl, n-butyl, sec-butyl, isobutyl, tert-butyl, n-pentyl, 2-methylbutyl, 3-methylbutyl, 4-methylpentyl, neopentyl, n-hexyl, 1,2-dimethylpropyl, 2,2-dimethylpropyl and 1,2,2-trimethylpropyl.

The term "$C_{1-6}$-alkoxy" as used herein, alone or in combination, refers to a straight or branched monovalent substituent comprising a $C_{1-6}$-alkyl group linked through an ether oxygen having its free valence bond from the ether oxygen and having 1 to 6 carbon atoms e.g. methoxy, ethoxy, propoxy, isopropoxy, butoxy, pentoxy.

The term "halogen" means fluorine, chlorine, bromine or iodine.

In a preferred embodiment of the invention $R^1$, $R^{1a}$, $R^2$ and $R^{2a}$ are independently selected from hydrogen halogen, trifluoromethyl, $C_{1-6}$-alkyl or methylthio, preferably $R^1$, $R^{1a}$, $R^2$ and $R^{2a}$ are independently hydrogen, halogen, methyl or methylthio.

In a another preferred embodiment of the invention X is selected from ortho-phenylene, —O—, —S—, —(S=O)—, —$CH_2CH_2$—, —CH=CH—, —O—$CH_2$—O— or —$CH_2$—O—$CH_2$—, preferably X is —O— or —S—.

In another preferred embodiment of the invention Y is selected from Y is —O— or —$S(O)_q$— wherein q is 0.

In another preferred embodiment of the invention r is 1 or 2.

In another preferred embodiment of the invention Z is selected from

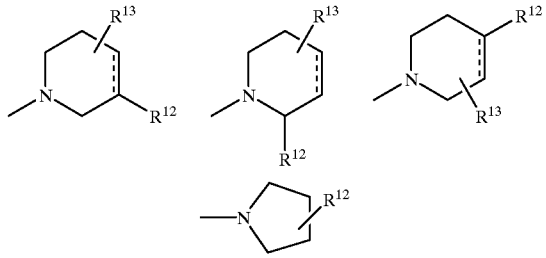

wherein $R^{12}$ and $R^{13}$ are as defined above.

In another preferred embodiment of the invention $R^{12}$ is —$(CH_2)_pCOR^{17}$ wherein p is 0 or 1 and $R^{17}$ is —OH.

In yet another preferred embodiment of the invention $R^{13}$ is hydrogen.

Illustrative examples of compounds encompassed by the present invention include:

1-(2-( 10,11-Dihydrodibenzo[b,f]thiepin-10-yloxy)-1-ethyl)-(3R)-piperidinecarboxylic acid;

1-(2-(2-Chloro-10,11-dihydrodibenzo[b,f]thiepin-10-yloxy)-1-ethyl)-3-piperidinecarboxylic acid;

1-(2-(2-Chloro-10,11-dihydrodibenzo[b,f]thiepin-10-yloxy)-1-ethyl)-4-piperidinecarboxylic acid;

1-(2-(2-Methyl-10,11-dihydrodibenzo[b,f]thiepin-10-yloxy)-1-ethyl)-4-piperidinecarboxylic acid;

1-(2-(2-Methyl-10,11-dihydrodibenzo[b,f]thiepin-10-yloxy)-1-ethyl)-3-piperidinecarboxylic acid;

1-(2-(8-Chloro-10,11-dihydrodibenzo[b,f]thiepin-10-yloxy)-1-ethyl)-3-piperidinecarboxylic acid;

1-(2-(8-Methylthio-10,11-dihydrodibenzo[b,f]thiepin-10-yloxy)-1-ethyl)-3-piperidinecarboxylic acid;

(R)-1-(2-(10,11-Dihydrodibenzo[b,f]oxepin-10-yloxy)ethyl)-3-piperidinecarboxylic acid;

(R)-1-(2-(2-Chloro-10,11-dihydrodibenzo[b,f]thiepin-10-ylsulfanyl)ethyl)-3-piperidinecarboxylic acid;

(R)-1-(11H-Dibenz[b,f][1,4]oxathiepin-11-ylmethyl)-3-piperidinecarboxylic acid;

(R)-1-(2-(2-Chloro-7-fluoro-10,11-dihydrodibenzo[b,f]thiepin-10-yloxy)ethyl)-3-piperidinecarboxylic acid;

(R)-1-(2-(2,4-Dichloro-10,11-dihydrodibenzo[b,f]thiepin-10-yloxy)ethyl)-3-piperidinecarboxylic acid;

or a pharmaceutically acceptable salt thereof.

It has been demonstrated that the novel compounds of formula I inhibit neurogenic inflammation which involves the release of neuropeptides from peripheral and central endings of sensory C-fibres. Experimentally this can be demonstrated in animal models of histamine induced paw oedema (Amann et al, Europ. J. Pharmacol. 279, 227–231, 1995) in which the novel compounds of formula I exhibit a potent inhibitory effect. Compounds of formula I may be used to treat all painful, hyperalgesic and/or inflammatory conditions in which C-fibres play a pathophysiological role by eliciting neurogenic pain or inflammation, i.e.:

Acutely painful conditions exemplified by migraine, postoperative pain, burns, bruises, post-herpetic pain (Zoster) and pain as it is generally associated with acute inflammation; chronic, painful and/or inflammatory conditions exemplified by various types of neuropathy (diabetic, post-traumatic, toxic), neuralgia, rheumatoid arthritis, spondylitis, gout, inflammatory bowel disease, prostatitis, cancer pain, chronic headache, coughing, asthma, itching, chronic pancreatitis, inflammatory skin disease including psoriasis and autoimmune dermatoses, osteoporotic pain.

Further, it has been demonstrated that the compounds of general formula I improve the glucose tolerance in diabetic ob/ob mice and that this may result from the reduced release of CGRP from peripheral nervous endings. Hence the compounds of general formula I may be used in the treatment of NIDDM as well as ageing-associated obesity. Experimentally this has been demonstrated by the subcutaneous administration of glucose into ob/ob mice with or without previous oral treatment with a compound of general formula I.

The compounds of formula I may be prepared by the following method:

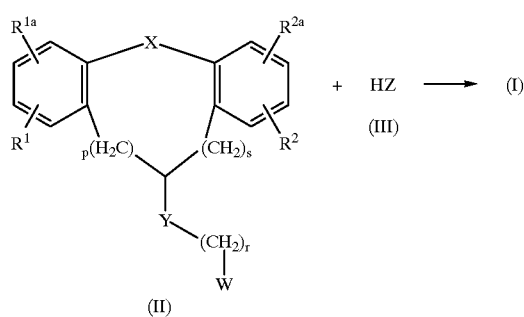

A compound of formula II wherein $R^1$, $R^{1a}$, $R^2$, $R^{2a}$, X, Y, r, p and s are as defined above and W is a suitable leaving group such as halogen, p-toluene sulphonate or mesylate may be reacted with an aza compound of formula Ill wherein Z is as defined above. This alkylation reaction may be carried out in a solvent such as acetone, dibutylether, 2-butanone, methyl ethyl ketone, ethyl acetate, tetrahydrofuran (THF) or toluene in the presence of a base e.g. sodium hydride or potassium carbonate and a catalyst, e.g. an alkali metal iodide at a temperature up to reflux temperature for the solvent used for e.g. 1 to 120 h. If esters have been prepared in which $R^{17}$ is alkoxy, compounds of formula I wherein $R^{17}$ is OH may be prepared by hydrolysis of the ester group, preferably at room temperature in a mixture of an aqueous alkali metal hydroxide solution and an alcohol such as methanol or ethanol, for example, for about 0.5 to 6 h.

Compounds of formula II and III may readily be prepared by methods familiar to those skilled in the art.

Under certain circumstances it may be necessary to protect the intermediates used in the above methods e.g. a compound of formula III with suitable protecting groups. The carboxylic acid group can, for example, be esterified. Introduction and removal of such groups is described in "Protective Groups in Organic Chemistry" J. F. W. McOrnie ed. (New York, 1973).

PHARMACOLOGICAL METHODS

I. Histamine Induced Paw Oedema

The rat histamine paw oedema test was performed essentially as described by Amann et al. (Europ. J. Pharmacol. 279, 227–231, 1995). In brief 250–300 g male Sprague-Dawley rats were anaesthetized with pentobarbital sodium, and placed on a 32 degree (Celsius) heated table. Ten minutes later histamine (50 micoliter, 3 mg/ml) was injected in the right hind paw and 20 minutes hereafter the paw swelling was determined by water plethysmography (Ugo Basile). Test compounds were administered intraperitoneally at 15 minutes before the anaesthetics.

II. Reduced Release of CGRP ob/ob female mice, 16 weeks of age, where injected glucose (2 g/kg) subcutaneously. At times hereafter blood glucose was determined in tail venous blood by the glucose oxidase method. At the end of the study the animals were decapitated and trunk blood collected. Immunoreactive CGRP was determined in plasma by radio-immuno-assay. Two groups of animals were used. The one group was vehicle treated, whereas the other group received a compound of formula I via drinking water (100 mg/l) for five days before the test.

Values for inhibition of histamine induced oedema response for some representative compounds are recorded in table 1.

TABLE 1

| Inhibition of histamine induced pain response at 1.0 mg/kg | |
|---|---|
| Example no. | % Oedema inhibition |
| 1 | 37 |
| 5 | 49 |

PHARMACEUTICAL COMPOSITIONS

The present invention also relates to pharmaceutical compositions comprising a compound of formula I or a pharmaceutically acceptable salt thereof and, usually, such compositions also contain a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatine, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax. The route of administration may be any route which effectively transports the active compound to the appropriate or desired site of action, such as oral, nasal, pulmonary or parenteral e.g. rectal, depot, transdermal, subcutaneous, intranasal, intramuscular, topical, intravenous, intraurethral, ophthalmic solution or an ointment, the oral route being preferred.

If a solid carrier for oral administration is used, the preparation can be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilising agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil. Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques contains

| Core: | |
|---|---|
| Active compound (as free compound or salt thereof) | 100 mg |
| Colloidal silicon dioxide (Areosil ®) | 1.5 mg |
| Cellulose, microcryst. (Avicel ®) | 70 mg |
| Modified cellulose gum (Ac-Di-Sol ®) | 7.5 mg |
| Magnesium stearate | |
| Coating: | |
| HPMC | approx. 9 mg |
| *Mywacett ® 9-40 T | approx. 0.9 mg |

*Acylated monoglyceride used as plasticizer for film coating.

The compounds of the invention may be administered to a mammal, especially a human, in need of such treatment, prevention, elimination, alleviation, or amelioration of an indication related to all painful, hyperalgesic and/or inflammatory conditions in which C-fibres play a pathophysiological role such as e.g. neurogenic pain, inflammation, migraine, neuropathy, itching and rheumatoid arthritis, as well as indications caused by or related to the secretion and circulation of insulin antagonising peptides, such as non-insulin-dependent diabetes mellitus (NIDDM) or ageing-associated obesity. Such mammals include also animals, both domestic animals, e.g. household pets, and non-domestic animals such as wildlife.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

For the above indications the dosage will vary depending on the compound of formula I employed, on the mode of administration and on the therapy desired. However, in general, satisfactory results are obtained with a dosage of from about 0.5 mg to about 1000 mg, preferably from about 1 mg to about 500 mg of compounds of formula I, conveniently given from 1 to 5 times daily, optionally in sustained release form. Usually, dosage forms suitable for oral administration comprise from about 0.5 mg to about 1000 mg, preferably from about 1 mg to about 500 mg of the compounds of formula I admixed with a pharmaceutical carrier or diluent.

Suitable dosage ranges varies as indicated above depending as usual upon the exact mode of administration, form in which administered, the indication towards which the administration is directed, the subject involved and the body weight of the subject involved, and the preference and experience of the physician or veterinarian in charge.

Generally, the compounds of this invention are dispensed in unit dosage form comprising 50–200 mg of active ingredient in or together with a pharmaceutically acceptable carrier per unit dosage.

Usually, dosage forms suitable for oral, nasal, pulmonal or transdermal administration comprise from about 0.5 mg to about 1000 mg, preferably from about 1 mg to about 500 mg of the compounds of formula I admixed with a pharmaceutically acceptable carrier or diluent.

Any novel feature or combination of features described herein is considered essential to this invention.

EXAMPLES

The process for preparing compounds of formula I and preparations containing them is further illustrated in the following examples, which, however, are not to be construed as limiting.

Hereinafter, TLC is thin layer chromatography and wherever it is stated that chloroform is used as eluent or part of an eluent mixture in TLC, the eluent that has been used is chloroform saturated with ammonia. $CDCl_3$ is deutero chloroform and DMSO-$d_6$ is hexadeutero dimethylsulfoxide. The structures of the compounds are confirmed by either elemental analysis or NMR, where peaks assigned to characteristic protons in the title compounds are presented where appropriate. $^1$H NMR shifts ($\delta_H$) are given in parts per million (ppm). M.p. is melting point and is given in ° C. and is not corrected. Column chromatography was carried out using the technique described by W. C. Still et al, J. Org. Chem. (1978), 43, 2923–2925 on Merck silica gel 60 (Art. 9385). Compounds used as starting materials are either known compounds or compounds which can readily be prepared by methods known per se.

Example 1

1-(2-(10,11-Dihydrodibenzo[b,f]thiepin-10-yloxy)-1-ethyl)-(3R)-piperidinecarboxylic acid acetate

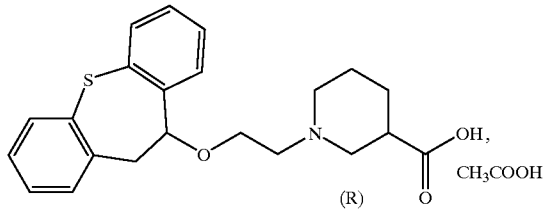

10-Chloro-10,11-dihydrodibenzo[b,f]thiepine (10 g, 0.041 mol, prepared as described in Monatshefte 96, 182, 1965) was slowly added to a mixture of 2-bromoethanol (44 g, 0.35 mol) and powdered potassium carbonate (10 g, 0.072 mol) at room temperature. After stirring for 6 h, dichloromethane (15 ml) was added, and the reaction mixture was heated at 50° C. for 3 h. After cooling, dichloromethane (35 ml) was added and the mixture was filtered. The dichloromethane was evaporated and excess of 2-bromoethanol was distilled off in vacuo. The oily residue was dissolved in benzene (100 ml), washed with water (3×70 ml), dried ($K_2CO_3$) and the solvent was evaporated to give 13.8 g of crude 10-(2-bromoethoxy)-10,11-dihydrodibenzo[b,f]thiepine as an oil.

A mixture of the above crude bromide (6.1 g, 0.018 mol), (R)-3-piperidinecarboxylic acid ethyl ester tartrate (6.0 g, 0.02 mol), potassium carbonate (8.2 g, 0.06 mol) and acetone (100 ml) was heated at reflux temperature under stirring for 20 h. The mixture was filtered and the solvent evaporated in vacuo. The oily residue was purified by chromatography on silica gel using benzene as eluent to give 5.3 g of 1-(2-(10,11-dihydrodibenzo[b,f]thiepin-10-yloxy)-1-ethyl)-(3R)-piperidinecarboxylic acid ethyl ester as an oil.

TLC: $R_f$=0.45 ($SiO_2$: chloroform)

The above ester (4.9 g, 0.0119 mol) was dissolved in ethanol (30 ml) and 5 N sodium hydroxide (5 ml) was added. The mixture was stirred at room temperature for 20 h, and ethanol was evaporated in vacuo. Water (50 ml) followed by acetic acid (7 ml) were added, and the mixture was extracted with dichloromethane (100 ml). The organic phase was dried ($MgSO_4$) and the solvent was evaporated in vacuo. The residue was triturated with diethyl ether and the solid was isolated by filtration and dried to give 4.0 g (76%) of the title compound as an amorphous solid.

M.p. 82–89° C.

Calculated for $C_{22}H_{25}NO_3S$, $CH_3COOH$:

C, 64.99%; H, 6.59%; N, 3,16%; S, 7.23%; Found: C, 65.13%; H, 6.49%; N, 2.99%, S, 7.48%.

Example 2

1-(2-(2-Chloro-10,11-dihydrodibenzo[b,f]thiepin-10-yloxy)-1-ethyl)-3-piperidinecarboxylic acid hydrogen oxalate

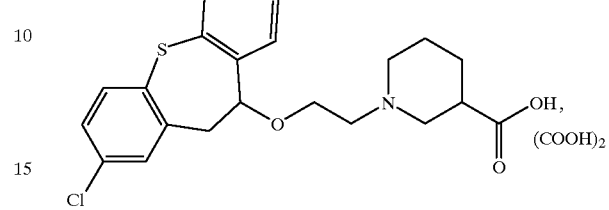

To a mixture of 2-chloro-10,11-dihydrodibenzo[b,f]thiepin-10-ol (10 g, 38 mmol, prepared similarly as described in Coll. Czech. Chem. Commun. 33, 1852, 1968), 2-bromoethanol (7.5 g, 60 mmol) and potassium carbonate (5 g, 38 mmol) in absolute benzene (100 ml), boron trifluoride etherate (5.7 g, 40 mmol) was dropwise added at 10–14° C., and stirring was continued at 10–14° C. for 1.5 h. The mixture was cooled to 10° C., and cold water (50 ml) was added dropwise. The organic layer was separated, washed with water (3×50 ml) and dried ($Na_2SO_4$). The solvent was evaporated in vacuo, and the residual oil (12.9 g, 92%) was used without further purification in the next step.

A mixture of the above bromide (11.2 g, 29 mmol), 3-piperidinecarboxylic acid ethyl ester (4.7 g, 30 mmol) and potassium carbonate (8.3 g, 60 mol) in N,N-dimetylformamide (50 ml) was heated for 6 h at 60° C. After cooling, water (150 ml) and toluene (150 ml) were added, the phases were separated, and the aqueous phase was extracted with toluene (100 ml). The combined organic phases were dried ($K_2CO_3$ and $Na_2SO_4$), and the solvent was evaporated in vacuo. The oily residue (13.6 g) was purified by column chromatography on silica gel, using benzene as eluent. This afforded 9.05 g (68%) of 1-(2-(2-chloro-10,11-dihydrodibenzo[b,f]thiepin-10-yloxy)-1-ethyl)-3-piperidinecarboxylic acid ethyl ester.

TLC: $R_f$=0.5 ($SiO_2$: chloroform)

To the above ester (2.63 g, 6 mmol) in ethanol (10 ml), a solution of potassium hydroxide (0.85 g, 15 mmol) in water (5 ml) was added, and the resulting mixture was heated at reflux temperature for 3.5 h. Ethanol was evaporated in vacuo, and water (20 ml) and acetic acid (1 ml), were added. The mixture was extracted with chloroform (2×15 ml), the organic extracts were dried ($Na_2SO_4$) and evaporated in vacuo. The residue (2.7 g) was transformed into the corresponding hydrogen oxalate.

M.p. 95–99° C.

Calculated for $C_{22}H_{24}ClNO_3S$, $(COOH)_2$:

C, 56.74%; H, 5.16%; Cl, 6.98%; N, 2.76%; S, 6.31%; Found: C, 56.88%; H, 5.19%; Cl, 7.00%; N, 2.72%; S, 6.60%.

Example 3

1-(2-(2-Chloro-10,11-dihydrodibenzo[b,f]thiepin-10-yloxy)-1-ethyl)-4-piperidinecarboxylic acid hydrogen oxalate

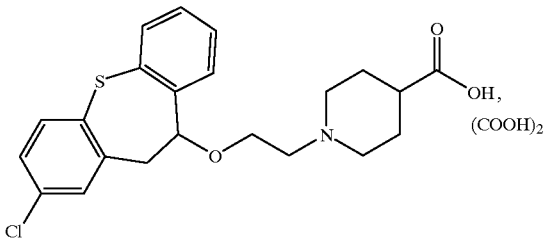

A mixture of 10-(2-bromoethoxy)-2-chloro-10,11-dihydrodibenzo[b,f]thiepine (5.19 g, 14 mmol, prepared similarly as described in example 2), 4-piperidinecarboxylic acid ethyl ester (2.20 g, 14 mmol) and anhydrous potassium carbonate (4.70 g, 34 mmol) in dry N,N-dimethylformamide (25 ml) was stirred at 60–66° C. for 6 h. After standing overnight at room temperature, benzene (50 ml) and water (50 ml) were added, and the phases were separated. The organic layer was washed with water (2×50 ml), dried ($K_2CO_3$) and evaporated in vacuo. The oily residue was purified by column chromatography on silica gel using benzene as eluent, affording 4.28 g (68%) of oily 1-(2-(2-chloro-10,11-dihydrodibenzo[b,f]thiepin-10-yloxy)-1-ethyl)-4-piperidinecarboxylic acid ethyl ester. The oil was dissolved in dry acetone (40 ml), oxalic acid dihydrate (1.76 g, 14 mmol) and ether were added, and the formed hydrogen oxalate was crystallised from a mixture of acetone and ether.

TLC: $R_f$=0.4 ($SiO_2$: chloroform/methanol=150:1)

To a solution of the above ethyl ester hydrogen oxalate (2.0 g, 3.73 mmol) in ethanol (15 ml), potassium hydroxide (13%, 7 ml) was added and the mixture was heated at reflux temperature for 3.5 h. Ethanol was evaporated, the residue dissolved in water (20 ml), and pH was adjusted with acetic acid to 5.5. The mixture was extracted with chloroform (45 ml), the organic layer was dried ($Na_2SO_4$) and evaporated in vacuo. The oily residue was dissolved in acetone (15 ml) and afforded after treatment with oxalic acid (0.50 g, 4 mmol) 1.55 g (81%) of the title compound.

M.p. 114–117° C.

Calculated for $C_{22}H_{24}ClNO_3S$, 0.5 $H_2O$, $(COOH)_2$:

C, 55.75%; H, 5.26%; Cl, 6.86%; N, 2.71%; S, 6.20%; Found: C, 55.57%; H, 5.18%; Cl, 6.86%; N, 2.76%; S, 6.14%.

Example 4

1-(2-(2-Methyl-10,11-dihydrodibenzo[b,f]thiepin-10-yloxy)-1-ethyl)-4-piperidinecarboxylic acid hydrogen oxalate

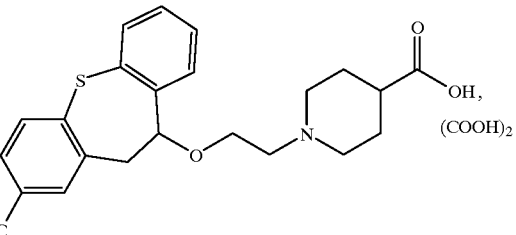

To a solution of 2-methyl-10,11-dihydrodibenzo[b,f]thiepin-10-ol (3.63 g, 15 mmol, prepared as described in Ger. Offen. 2,336,130, 1974) and 2-bromoethanol (2.5 g, 20 mmol) in absolute benzene (25 ml), a solution of boron trifluoride etherate (2.25 g. 15.8 mmol) in absolute benzene (10 ml) was dropwise added at 10–15° C. over 15 minutes. The reaction mixture was stirred at 10–15° C. for 2 h and water (18 ml) was added. The organic layer was separated, washed with water (2×25 ml), dried ($Na_2SO_4$) and evaporated in vacuo to give 3.83 g (73%) crude 10-(2-bromoethoxy)-2-methyl-10,11-dihydrodibenzo[b,f]thiepine, which was used without further purification in the next step.

The above bromide (3.83 g, 11 mmol), 4-piperidinecarboxylic acid ethyl ester (1.71 g, 11 mmol) and potassium carbonate (3.04 g, 22 mmol) in dry N,N-dimethylformamide (16 ml) were stirred for 1 h at room temperature, and then for 4 h at 40° C. The reaction mixture was diluted with benzene (100 ml), washed with water (2×50 ml), and the organic layer was dried ($K_2CO_3$). After evaporation in vacuo, the oily residue was purified by column chromatography on silica gel using benzene as eluent. This afforded 4.28 g (68%) of 1-(2-(2-methyl-10,11-dihydrodibenzo[b,f]thiepin-10-yloxy)-1-ethyl)-4-piperidinecarboxylic acid ethyl ester as an oil. The ethyl ester (4.28 g, 9.3 mmol) was dissolved in acetone (9 ml) and oxalic acid dihydrate (0.26 g) was added. The mixture was heated shortly at reflux temperature. After cooling, the precipitate was filtered off and recrystallised from a mixture of acetone and diethyl ether, to give 2.38 g (40%) of the hydrogen oxalate.

TLC: $R_f$=0.6 ($SiO_2$: chloroform/methanol=150:1)

A mixture of the above ester hydrogen oxalate (1.03 g, 2 mmol) in ethanol (9 ml) and a 16% solution of potassium hydroxide (3.6 ml) was heated at reflux temperature for 4 h. Ethanol was evaporated in vacuo and the residue was dissolved in water (15 ml). pH was adjusted to 5.5 with acetic acid (1 ml) and the mixture was extracted with chloroform (30 ml). The organic layer was washed with water (4×10 ml), dried ($Na_2SO_4$) and evaporated in vacuo. The residual amorphous solid (0.79 g, 99%) was dissolved in acetone (7.5 ml), oxalic acid dihydrate (0.26 g) was added at 40° C. and the mixture was left to stay overnight. The precipitate was filtered off and recrystallised from acetone to give the title compound.

M.p. 112–116° C.

Calculated for $C_{23}H_{27}NO_3S$, $(COOH)_2$:

C, 61.58%; H, 5.99%; N, 2.87%; S, 6.58%; Found: C, 61.11%; H, 5.96%; N, 2.74%; S, 6.48%.

Example 5

1-(2-(2-Methyl-10,11-dihydrodibenzo[b,f]thiepin-10-yloxy)-1-ethyl)-3-piperidinecarboxylic acid hydrogen oxalate

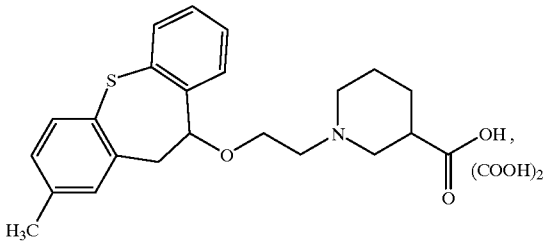

A mixture of 10-(2-bromoethoxy)-2-methyl-10,11-dihydrodibenzo[b,f]thiepine (3.41 g, 9 mmol, prepared as described in example 4), 3-piperidinecarboxylic acid ethyl ester (1.41 g, 9 mmol) and anhydrous potassium carbonate (2.5 g, 18 mmol) in N,N-dimethylformamide (14 ml) was stirred at 50° C. for 8 h, and left to stay overnight. After cooling, benzene (40 ml) and water (90 ml) were added, and the phases were separated. The organic phase was treated with charcoal, dried ($Na_2SO_4$) and evaporated in vacuo. The oily residue (3.85 g) was purified by column chromatography on silica gel using benzene as eluent. This afforded 2.6 g (68%) of 1-(2-(2-methyl-10,11-dihydrodibenzo[b,f]thiepin-10-yloxy)-1-ethyl)-3-piperidinecarboxylic acid ethyl ester as an oil. The ethyl ester (2.6 g, 6.1 mmol) was dissolved in acetone (9 ml), oxalic acid dihydrate (0.77 g, 6.1 mmol) was added, and the mixture was heated to 40° C. After cooling, the resulting precipitate was filtered off and recrystallised from a mixture of acetone (50 ml) and ethanol (20 ml) to give 1.28 g (33%) of the hydrogen oxalate.

TLC: $R_f$=0.45 ($SiO_2$: chloroform/methanol=150:1)

A mixture of the above ester hydrogen oxalate (1.03 g, 2 mmol) in ethanol (9 ml) and a 14% solution of potassium hydroxide (4.6 ml) was stirred at reflux temperature for 6.5 h. Ethanol was evaporated, the residue was dissolved in water (15 ml) and acidified with acetic acid (1.5 ml) to pH 5.5. The solution was extracted with chloroform (80 ml), washed with water (15 ml), dried ($Na_2SO_4$) and evaporated in vacuo. The oily residue was dissolved in hot acetone (20 ml) and oxalic acid dihydrate (0.265 g, 2.1 mmol) was added. After cooling, ether (20 ml) was added. The precipitate was filtered off and crystallised from a mixture of 2-propanol and ether. Yield 0.82 g (84%) of the title compound.

M.p. 102–104° C.

Calculated for $C_{23}H_{27}NO_3S$, 0.5 $H_2O$, $(COOH)_2$:

C, 60.46%; H, 6.09%; N, 2.82%; S, 6.46%; Found: C, 60.50%; H, 6.05%; N, 2.69%; S, 6.85%.

Example 6

1-(2-(8-Chloro-10,11-dihydrodibenzo[b,f]thiepin-10-yloxy)-1-ethyl)-3-piperidinecarboxylic acid hydrogen oxalate

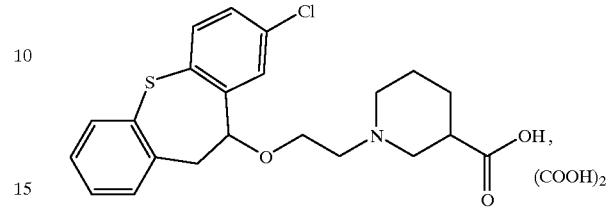

8,10-Dichloro-10,11-dihydrodibenzo[b,f]thiepine (10 g, 35.6 mmol, prepared as described in Coll. Czech. Chem. Commun. 33,183, 1968) was slowly added to a mixture of 2-bromoethanol (44 g, 0.352 mol) and powdered potassium carbonate (10 g, 0.072 mol) at 20° C. under stirring. After 6 h, dichloromethane (15 ml) was added and the reaction mixture was heated at 50° C. for 3 h. After cooling, dichloromethane (35 ml) was added and the mixture was filtered. Dichloromethane was evaporated and excess of 2-bromoethanol was distilled off in vacuo. The oily residue was dissolved in benzene (100 ml), washed with water (3×70 ml), dried ($K_2CO_3$) and the solvent evaporated to give 13.0 g of crude 8-chloro-10-(2-bromoethoxy)-10,11-dihydrodibenzo[b,f]thiepine as an oil.

A mixture of the above crude bromide (12.1 g, 32.7 mmol), 3-piperidinecarboxylic acid ethyl ester (5.0 g, 31.8 mmol), potassium carbonate (5.0 g, 36.2 mmol), potassium iodide (0.5 g) and acetone (100 ml) was heated at reflux temperature under stirring for 20 h. The mixture was filtered and the solvent evaporated in vacuo. The oily residue was purified by column chromatography on silica gel (100 g) using ethyl acetate as eluent to give 9.7 g of 1-(2-(8-chloro-10,11-dihydro-dibenzo[b,f]thiepin-10-yloxy)-1-ethyl)-3-piperidinecarboxylic acid ethyl ester as an oil.

TLC: $R_f$=0.50 ($SiO_2$: chloroform/methanol=150:1)

The above ester (5.4 g, 12.1 mmol) was dissolved in ethanol (50 ml), 5 N sodium hydroxide (5 ml) was added, and the mixture was stirred at room temperature for 20 h. Ethanol was evaporated in vacuo, water (50 ml) and acetic acid (7 ml) were added, and the mixture was extracted with dichloromethane (100 ml). The organic phase was dried ($MgSO_4$) and the solvent was evaporated in vacuo. The residue was dissolved in acetone and treated with oxalic acid to give 3.8 g (62%) of the title compound.

M.p. 190–192° C.

Calculated for $C_{22}H_{24}ClNO_3S$, $(COOH)_2$:

C, 56.74%; H, 5.16%; N, 2.76%; Cl, 6.98%; S, 6.31%; Found: C, 56.86%; H, 5.33%; N, 2.59%; Cl, 6.87%; S, 6.31%.

Example 7

1-(2-(8-Methylthio-10,11-dihydrodibenzo[b,f]thiepin-10-yloxy)-1-ethyl)-3-piperidinecarboxylic acid hydrogen oxalate

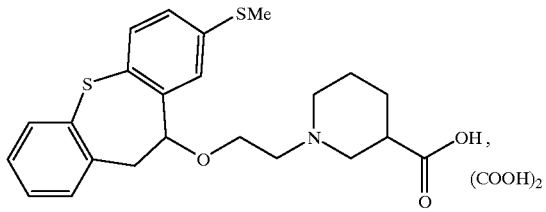

The title compound was prepared analogously as described for the title compound in example 6, using 8-methylthio-10-chloro-10,11-dihydrodibenzo[b,f]thiepine (10 g, 34.1 mmol, prepared as described in Coll. Czech. Chem. Commun. 33, 1895, 1968) as starting material.

M.p. 166–169° C.

Calculated for $C_{23}H_{27}NO_3S_2$, $(COOH)_2$:

C, 57.78%; H, 5.63%; N, 2.70%; S, 12.34%; Found: C, 57.55%; H, 5.62%; N, 2.44%; S, 12.00%.

Example 8

(R)-1-(2-(10,11-Dihydrodibenzo[b,f]oxepin-10-yloxy)ethyl)-3-piperidinecarboxylic acid hydrochloride

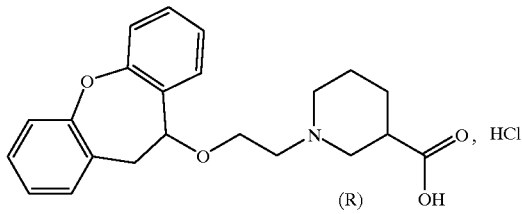

At 10–15° C., and over 15 minutes, a solution of boron trifluoride ethyl etherate (1.66 g, 11.6 mmol) in dry benzene (5 ml) was added dropwise to a stirred solution of 10,11-dihydrodibenz[b,f]oxepin-10-ol (2.29 g, 10.8 mmol, prepared as described in Coll. Czech. Chem. Commun.34, 2258 (1969) ) and 2-bromoethanol (2.13 g, 17 mmol) in dry benzene (20 ml). Stirring was continued at 10–15° C. for 1.5 h. The reaction mixture was quenched with cold water (15° C., 15 ml), the organic phase was washed with water (3×30 ml), dried (sodium sulfate) and evaporated in vacuo. The residual oily raw product (2.77 g), 10-(2-bromoethoxy)-10,11-dihydrodibenz[b,f]oxepine was used without further purification in the next reaction step.

A mixture of the above bromide (2.77 g, 8.7 mmol), (R)-3-piperidinecarboxylic acid ethyl ester tartrate (1.42 g, 9 mmol) and powdered potassium carbonate (1.56 g, 10 mmol) in dry N,N-dimethylformamide (15 ml) was stirred, first at 40–48° C. for 7 h and then at room temperature overnight. The mixture was diluted with benzene (80 ml) and washed with water (3×30 ml). The organic layer was dried (potassium carbonate) and evaporated in vacuo. The oily residue (3.31 g) was purified by column chromatography on silica gel (70 g), using first benzene and then chloroform as eluents. The chloroform fraction contained 1.75 g (54%) of (R)-1-(2-(10,11-dihydrodibenzo[b,f]oxepin-10-yloxy)ethyl)-3-piperidinecarboxylic acid ethyl ester.

TLC: $R_f$=0.3 ($SiO_2$: chloroform saturated with ammonia/methanol=100:1).

Under stirring at room temperature, a solution of the above ethyl ester (1.7 g, 4.3 mmol) in ethanol (17 ml) was treated with 4 N sodium hydroxide (11 ml, 43 mmol) for 20 h. Ethanol was evaporated and the oily residue was dissolved in water (80 ml). The solution was extracted with ether (3×50 ml), and the aqueous layer was filtered first with charcoal (0.5 g) and then on silica gel (2 g). Dichloromethane (350 ml) was added and the mixture was acidified to pH 1 using 6 N hydrochloric acid (7.5 ml). The organic layer was dried ($MgSO_4$), evaporated in vacuo and stripped with dry acetone (2×20 ml) twice. The crude product (1.3 g) was dissolved in dry acetone (20 ml) and dropwise added very slowly into vigorously stirred dry ether (150 ml). The mixture was stirred for 1 h at room temperature. The precipitate was filtered off, washed with dry ether (4×25 ml) and dried to give 1.27 g (73%) of the title compound.

M.p. 106–112° C.

Calculated for $C_{22}H_{25}NO_4$, HCl, 0.5 $H_2O$:

C, 63.99%; H, 6.59%; N, 3.39%; Cl, 8.59%, Found: C, 63.93%; H, 6.57%; N, 3.17%; Cl, 8.29%.

Example 9

(R)-1-(2-(2-Chloro-10,11-dihydrodibenzo[b,f]thiepin-10-ylsulfanyl)ethyl)-3-piperidinecarboxylic acid hydrochloride

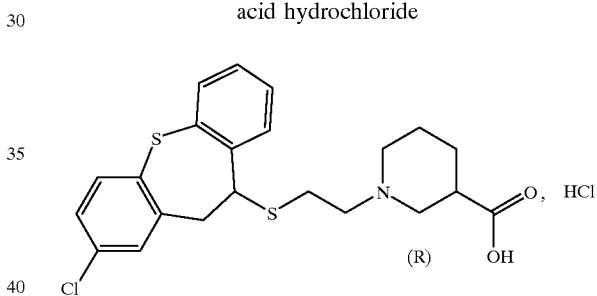

To a solution of sodium ethoxide (prepared by dissolving sodium (0.3 g, 13 mmol) in dry ethanol (20 ml) ), 2-chloro-10,11-dihydrodibenzo[b,f]thiepin-10-ylthiol (3.6 g, 13 mmol, prepared as described in Coll. Czech. Chem. Commun. 54, 1403, 1989) was added and the mixture was stirred for 30 minutes at 60° C. 2-Bromoethanol (2.0 g,16 mmol) was added and the mixture was heated at reflux temperature for 2 h. Ethanol was evaporated and benzene (60 ml) and water (25 ml) were added. The organic phase was separated and washed with 1 M potassium carbonate (3×20 ml) and water (3×30 ml) to pH 6.5, dried (potassium carbonate) and evaporated in vacuo. The residual oil (4.5 g) was purified by column chromatography on silica gel (100 g) using benzene as eluent, affording 2-(2-chloro-10,11-dihydrodibenzo[b,f]thiepin-10-yl-sulfanyl)ethanol in quantitative yield.

TLC: $R_f$=0.46 ($SiO_2$: chloroform).

A solution of methanesulfonyl chloride (2.02 g, 20 mmol) in dry toluene (20 ml) was added dropwise to a solution of the above alcohol (4.16 g, 12.9 mmol) in dry toluene (100 ml) and triethylamine (4.05 g, 40 mmol) at 8–15° C., over 0.5 h. Stirring was continued for 0.5 h at 8–15° C. and then at room temperature for 6 h. The mixture was washed with water (4×100 ml), dried (sodium sulfate) and evaporated in vacuo, to give the corresponding mesylate in quantitative yield as an oil.

To a solution of the above mesylate (5.16 g, 12.8 mmol) in dry acetone (100 ml), (R)-3-piperidinecarboxylic acid ethyl ester tartrate (2.26 g, 14.4 mmol) and potassium carbonate (2.1 g, 15 mmol) were added. The reaction mixture was stirred at room temperature overnight and then at reflux temperature for 5 h. After cooling, the precipitate was filtered off and the filtrate was evaporated in vacuo. The residue (6.45 g) was purified by column chromatography on silica gel (150 g), using first benzene and then chloroform as eluents, affording 4.24 g (71%) of (R)-1-(2-(dibenzo[b,f] thiepin-10-ylsulfanyl)ethyl)-3-piperidinecarboxylic acid ethyl ester.

TLC: $R_f$=0.18 (SiO$_2$: chloroform).

The free base was treated with oxalic acid dihydrate (1.26 g, 10 mmol) in dry acetone (25 ml), affording, after recrystallisation from 2-propanol, 3.9 g (69%) of the ethyl ester hydrogen oxalate.

A mixture of the above ethyl ester hydrogen oxalate (3.3 g, 6 mmol) in ethanol (35 ml) and 4 N sodium hydroxide (15 ml, 60 mmol) was stirred overnight at room temperature and then for 0.5 h at reflux temperature. After cooling to 15° C., dichloromethane was added and the mixture was acidified using 6 N hydrochloric acid (12 ml) to pH 1. The organic layer was separated, dried (MgSO$_4$) and evaporated in vacuo. The solid residue was triturated with a 1:1 mixture of acetone and ether (50 ml), filtered off and washed with dry ether (2×25 ml), to give 2.44 g (94%) of the title compound.

M.p. 220–224° C. (ethanol/diethyl ether).

Calculated for C$_{22}$H$_{24}$ClNO$_2$S$_2$, HCl:
C, 56.16%; H, 5.36%; Cl, 15.07%; N, 2.98%; S, 13.63%; Found: C, 56.35%; H, 5.65%; Cl, 15.04%; N, 2.68%; S, 13.31%.

Example 10

(R)-1-(11H-Dibenz[b,f][1,4]oxathiepin-11-ylmethyl)-3-piperidinecarboxylic acid hemimaleate

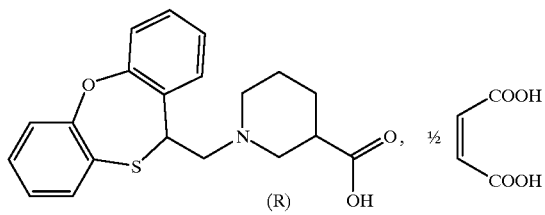

A mixture of 11-bromomethyl-11H-dibenz[b,f][1,4] oxathiepine (6.15 g, 20 mmol, prepared similarly as described in Coll. Czech. Chem. Commun. 50, 1484, 1985), (R)-3-piperidinecarboxylic acid ethyl ester tartrate (4.7 g, 30 mmol) and chloroform (10 ml) was warmed to achieve dissolution. The solution was then allowed to stand for 1 week at room temperature, and was subsequently heated at reflux temperature for 7 h. After cooling, the mixture was diluted with benzene and washed with 5% ammonia. The organic phase was dried (potassium carbonate) and evaporated. The residue was purified by column chromatography on silica gel (55 g) using first benzene and then diethyl ether as eluents to give 4.1 g (53%) of (R)-1-(11H-dibenz[b,f][1,4]oxathiepin-11-ylmethyl)-3-piperidinecarboxylic acid ethyl ester as an oil.

TLC: $R_f$=0.50 (SiO$_2$: chloroform/ethanol/ammonium hydroxide=20:1:0.005).

The above ester (4.1 g, 10.7 mmol) was dissolved in ethanol (70 ml) and 5 N sodium hydroxide (5 ml) was added. The mixture was allowed to stand for 3 days at room temperature, and then ethanol was evaporated in vacuo and water (50 ml) was added. The mixture was extracted with diethyl ether and the phases were separated. Acetic acid (4 ml) was added and the mixture was extracted with dichloromethane (5×50 ml). The combined organic extracts were dried (MgSO$_4$) and the solvent was evaporated in vacuo. The residue was dissolved in diethyl ether and neutralised with maleic acid in diethyl ether. The amorphous precipitate was filtered off and dried. This afforded 3.95 g (77%) of the title compound.

Calculated for C$_{20}$H$_{21}$NO$_3$S, 0.5 C$_4$H$_4$O$_4$, 0.5 H$_2$O:
C, 59.99%; H, 5.45%; N, 2.91%; S, 6.67%; Found: C, 60.19%; H, 5.64%; N, 2.67%; S, 6.54%.

Example 11

(R)-1-(2-(2-Chloro-7-fluoro-10,11-dihydrodibenzo [b,f]thiepin-10-yloxy)ethyl)-3-piperidinecarboxylic acid hydrochloride

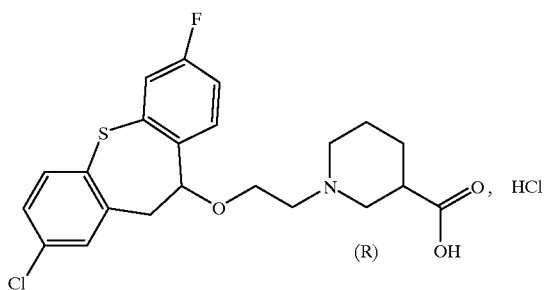

To a solution of 2,10-dichloro-7-fluoro-10,11-dihydrodibenzo[b,f]thiepine (4.14 g, 13.8 mmol, prepared as described in Coll. Czech. Chem. Commun. 40, 2887, 1975) in dichloromethane (24 ml), 2-bromoethanol (17.0 g, 136 mmol) was added, followed by dry potassium carbonate (6.25 g, 45 mmol). The reaction mixture was stirred at 40° C. for 11 h, additional dichloromethane (30 ml) was added, the inorganic salts were filtered off and the filtrate was evaporated in vacuo. This afforded 5.35 g (100%) of 10-(2-bromoethoxy)-2-chloro-7-fluoro-10,11-dihydrodibenzo[b,f] thiepine as an oil.

A mixture of the above bromide (5.35 g, 13.8 mmol), (R)-3-piperidinecarboxylic acid ethyl ester tartrate (2.5 g, 16 mmol) and potassium carbonate (3.0 g, 22 mmol) in N,N-dimethylformamide (25 ml) was stirred at 65–72° C. for 12 h and left to stand at room temperature overnight. The reaction mixture was diluted with benzene (150 ml) and washed with water (4×30 ml). The organic layer was dried (sodium sulfate) and evaporated in vacuo to give an oily residue (5.72 g), which was further purified by column chromatography on silica gel (100 g) using benzene and chloroform as eluents. The main fraction afforded 4.0 g (61%) of (R)-1-(2-(2-chloro-7-fluoro-10,11-dihydrodibenzo [b,f]thiepin-10-yloxy)ethyl)-3-piperidinecarboxylic acid ethyl ester as an oil.

TLC: $R_f$=0.52 (SiO$_2$: chloroform saturated with ammonia/ chloroform/methanol=5:1:0.02)

The free base (4.0 g, 8.6 mmol) was transformed to the corresponding hydrogen oxalate using oxalic acid dihydrate. (1.2 g, 9.3 mmol) in 2-propanol (10 ml) and ether (20 ml). Yield: 4.1 g (88%)

A mixture of the above ethyl ester hydrogen oxalate (2.2 g, 3.97 mmol) in 96% ethanol (22 ml) and 5 N sodium hydroxide (6 ml) was stirred at room temperature for 21 h. Ethanol was evaporated in vacuo, and the residue was dissolved in water (65 ml) and washed with diethyl ether (2×50 ml). Dichloromethane (250 ml) was added to the alkaline aqueous phase and the mixture was acidified with 5 N hydrochloric acid to pH 1. After stirring for 15 minutes, the organic layer was separated, dried (MgSO$_4$) and evaporated in vacuo. The residue was triturated with a mixture of acetone and ether (1:1) (3×25 ml). The solid product was filtered off and washed with ether (2×10 ml), affording 1.24 g (53%) of the title compound.

M.p. 130–134° C.

Calculated for C$_{22}$H$_{23}$ClFNO$_3$S, HCl, 0.5 H$_2$O:

C, 54.89%; H, 5.23%; N, 2.91%; Cl, 14.73%; F, 3.95%; S, 6.66%; Found: C, 55.17%; H, 5.29%; N, 2.74%; Cl, 14.43%; F, 4.05%; S, 6.72%.

Example 12

(R)-1-(2-(2,4-Dichloro-10,11-dihydrodibenzo[b,f]thiepin-10-yloxy)ethyl)-3-piperidinecarboxylic acid hydrochloride

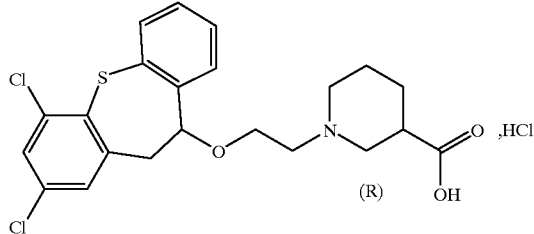

A mixture of 2,4,10-trichloro-10,11-dihydrodibenzo[b,f]thiepine (2.5 g, 8.6 mmol, prepared as described in Coll. Czech. Chem. Commun. 46, 781, 1981), 2-bromoethanol (12.5 g, 100 mmol) and potassium carbonate (4.0 g, 30 mmol) in dichloromethane (20 ml) was stirred at 40° C. for 11 h. The solid was filtered off and the filtrate was evaporated in vacuo. The residue (3.4 g) was dissolved in a mixture of diethyl ether and light petroleum (1:1) (40 ml) and left to stand in a refrigerator for a week, affording after isolation 2.6 g (80%) of 10-(2-bromoethoxy)-2,4-dichloro-10,11-dihydrodibenzo[b,f]thiepine.

A mixture of the above bromide (2.5 g, 6.2 mmol), (R)-3-piperidinecarboxylic acid ethyl ester tartrate (1.7 g, 11 mmol) and dry potassium carbonate (2.8 g, 20 mmol) in N,N-dimethylformamide (15 ml) was stirred at 50° C. for 18 h, diluted with benzene (60 ml), washed with water (5×30 ml), dried (sodium sulfate) and evaporated in vacuo. The oily residue (3.68 g) was purified by column chromatography on silica (70 g) using benzene and chloroform as eluents. This afforded 2.63 g (89%) of (R)-1-(2-(2,4-dichloro-10,11-dihydrodibenzo[b,f]thiepin-10-yloxy)ethyl)-3-piperidinecarboxylic acid ethyl ester as an oil.

TLC: R$_f$=0.64 (SiO$_2$: chloroform saturated with ammonia/methanol=300:1).

The free base was transformed to the corresponding hydrogen oxalate by treatment with oxalic acid dihydrate (0.76 g, 6 mmol) in 2-propanol (3 ml) and ether (14 ml). This afforded 1.7 g (48%) of the hydrogen oxalate.

A mixture of the above ethyl ester hydrogen oxalate (1.58 g, 2.77 mmol), 96% ethanol (16 ml) and 5 N sodium hydroxide (4 ml) was stirred at 40° C. for 4 h and then overnight at room temperature. Dichloromethane (250 ml) was added, followed by 5 N hydrochloric acid (4 ml) to pH 1. After stirring for 15 minutes, the organic layer was separated, dried (MgSO$_4$) and evaporated in vacuo. The solid residue was triturated with a mixture of acetone and ether (1:1) (3×30 ml), filtered off and washed with dry ether (2×10 ml), affording 1.1 g (81%) of the title compound.

M.p. 168–172° C.

Calculated for C$_{22}$H$_{23}$Cl$_2$NO$_3$S, HCl, 0.25 H$_2$O:

C, 53.56%; H, 5.01%; N, 2.64%; Cl, 21.56%, S, 6.50%; Found: C, 53.66%; H, 5.02%; N, 2.73%; Cl, 21.14%, S, 6.61%.

We claim:
1. A compound of formula I

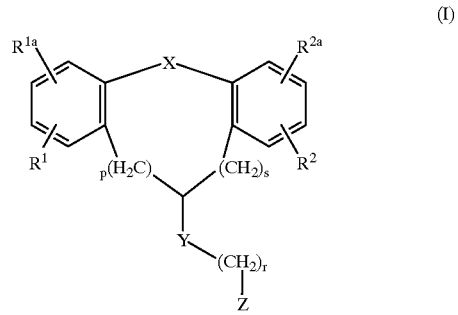

wherein

R$^1$, R$^{1a}$, R$^2$ and R$^{2a}$ independently are hydrogen, halogen, trifluoromethyl, hydroxy, C$_{1-6}$-alkyl, C$_{1-6}$-alkoxy or methylthio, —R$^7$R$^8$ or —SO$_2$NR$^7$R$^8$ wherein R$^7$ and R$^8$ independently are hydrogen or C$_{1-6}$-alkyl;

X is —O— or —S—;

Y is —O— or —S(O)$_q$— wherein q is 0, 1 or 2;

s is 0 and p is 1 or s is 1 and p is 0;

r is 1, 2, 3 or 4;

Z is one of the following groups:

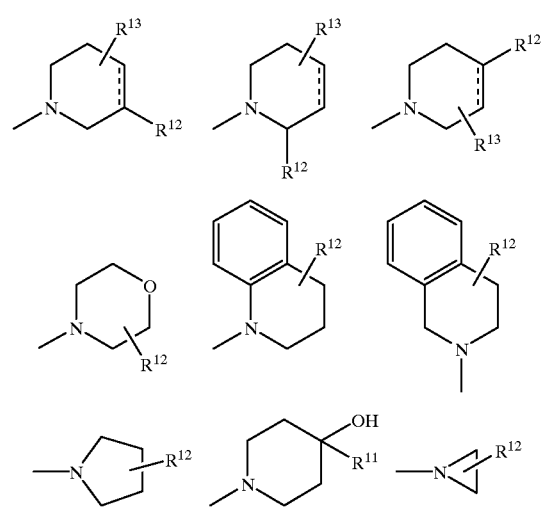

-continued

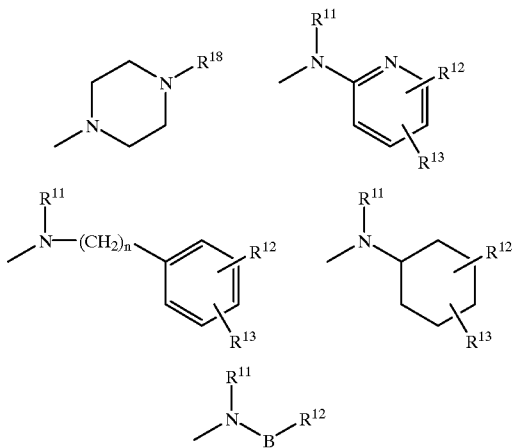

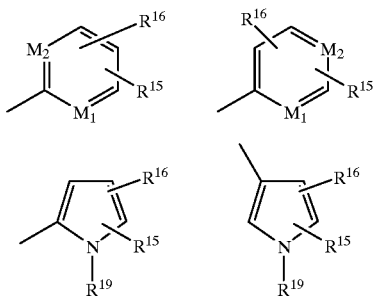

wherein n is 0, 1, or 2; $R^{11}$ is hydrogen, $C_{1-6}$-alkyl, $C_{1-6}$-alkoxy or phenyl optionally substituted with halogen, triflouromethyl, hydroxy, $C_{1-6}$-alkyl or $C_{1-6}$-alkoxy; $R^{12}$ is —(CH2)$_m$OH or —(CH$_2$)$_u$COR$^{17}$ wherein m is 0, 1, 2, 3, 4, 5 or 6 and u is 0 or 1 and $R^{17}$ is —OH, —NHR$^{20}$ or $C_{1-6}$-alkoxy, wherein $R^{20}$ is hydrogen or $C_{1-6}$-alkyl; $R^{13}$ is hydrogen, halogen, trifluoromethyl, hydroxy, $C_{1-6}$-alkyl or $C_{1-6}$-alkoxy; B is $C_{1-6}$-alkylene, $C_{2-6}$-alkenylene or $C_{2-6}$-alkynylene; . . . is optionally a single bond or a double bond; and $R^{18}$ is one of the following groups:

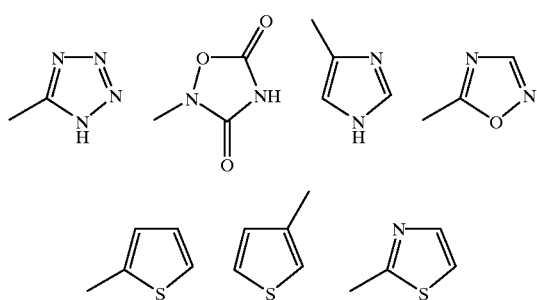

wherein $M_1$ and $M_2$ independently are C or N; $R^{19}$ is hydrogen, $C_{1-6}$-alkyl, phenyl or benzyl; $R^{15}$ is hydrogen, halogen, trifluoromethyl, nitro or cyano; $R^{16}$ is hydrogen, halogen, trifluoromethyl, nitro, cyano, —(CH$_2$)$_m$COR$^{17}$, —(CH$_2$)$_m$OH or —(CH$_2$)$_m$SO$_2$R$^{17}$, wherein m is 0, 1 or 2; or $R^{16}$ is one of the following groups:

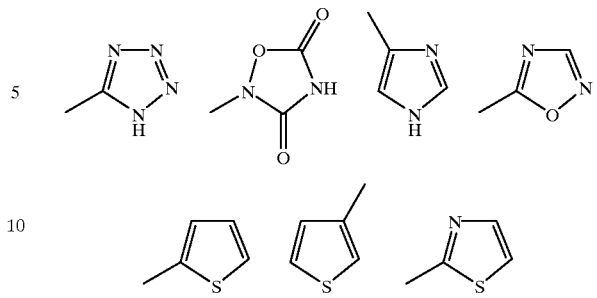

and $R^{21}$ is —(CH$_2$)$_n$COR$^{17}$, —(CH$_2$)$_n$OH or —(CH$_2$)$_n$SO$_2$R$^{17}$ wherein n is 0, 1, or 2; or $R^{21}$ is one of the following groups:

or a pharmaceutically acceptable salt thereof.

2. A compound of claim 1 wherein X is —O—.

3. A compound of claim 1 wherein X is —S—.

4. A compound of claim 2 wherein $R^1$, $R^{1a}$, $R^2$ and $R^{2a}$ independently are hydrogen, halogen, trifluoromethyl, $C_{1-6}$-alkyl or methylthio.

5. A compound of claim 2 wherein $R^1$, $R^{1a}$, $R^2$ and $R^{2a}$ independently are hydrogen, halogen, methyl or methylthio.

6. A compound of claim 2 wherein Y is —O— or —S(O)$_q$— wherein q is 0.

7. A compound of claim 2 wherein r is 1 or 2.

8. A compound of claim 2 wherein Z is one of the following groups:

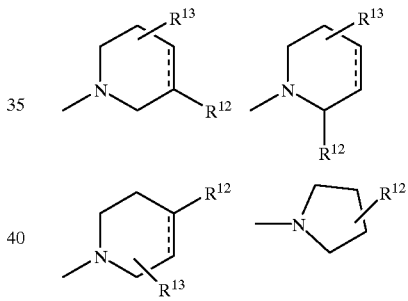

9. A compound of claim 2 wherein $R^{12}$ is —(CH$_2$)$_u$COR$^{17}$ wherein u is 0 or 1 and $R^{17}$ is OH.

10. A compound of claim 2 wherein $R^{13}$ is hydrogen.

11. A compound of claim 3 wherein $R^1$, $R^{1a}$, $R^2$ and $R^{2a}$ independently are hydrogen, halogen, trifluoromethyl, $C_{1-6}$-alkyl or methylthio.

12. A compound of claim 3, wherein $R^1$, $R^{1a}$, $R^2$ and $R^{2a}$ independently are hydrogen, halogen, methyl or methylthio.

13. A compound of claim 3 wherein Y is —O— or —S(O)$_q$— wherein q is 0.

14. A compound of claim 3 wherein r is 1 or 2.

15. A compound of claim 3 wherein Z is one of the following groups:

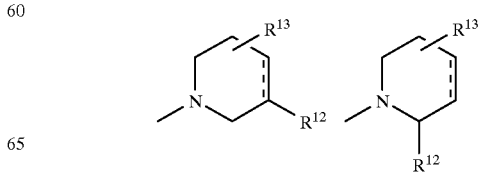

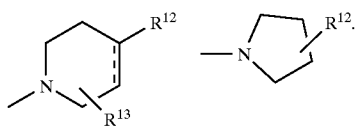

16. A compound of claim 3 wherein $R^{12}$ is —$(CH_2)_u$ $COR^{17}$ wherein u is 0 or 1 and $R^{17}$ is OH.

17. A compound of claim 3 wherein $R^{13}$ is hydrogen.

18. A compound of claim 1 which is:
1-(2-(10,11-Dihydrodibenzo[b,f]thiepin-10-yloxy)-1-ethyl)-(3R)-piperidinecarboxylic acid;
1-(2-(2-Chloro-10,11-dihydrodibenzo[b,f]thiepin-10-yloxy)-1-ethyl)-3-piperidinecarboxylic acid;
1-(2-(2-Chloro-10,11-dihydrodibenzo[b,f]thiepin-10-yloxy)-1-ethyl)-4-piperidinecarboxylic acid;
1-(2-(2-Methyl-10,11-dihydrodibenzo[b,f]thiepin-10-yloxy)-1-ethyl)-4-piperidinecarboxylic acid;
1-(2-(2-Methyl-10,11-dihydrodibenzo[b,f]thiepin-10-yloxy)-1-ethyl)-3-piperidinecarboxylic acid;
1-(2-(8-Chloro-10,11-dihydrodibenzo[b,f]thiepin-10-yloxy)-1-ethyl)-3-piperidinecarboxylic acid;
1-(2-(8-Methylthio-10,11-dihydrodibenzo[b,f]thiepin-10-yloxy)-1-ethyl)-3-piperidinecarboxylic acid;
(R)-1-(2-(2-Chloro-10,11-dihydrodibenzo[b,f]thiepin-10-ylsulfanyl)ethyl)-3-piperidinecarboxylic acid;
(R)-1-(2-(2-Chloro-7-fluoro-10,11-dihydrodibenzo[b,f]thiepin-10-yloxy)ethyl)-3-piperidinecarboxylic acid;
(R)-1-(2-(2,4-Dichloro-10,11-dihydrodibenzo[b,f]thiepin-10-yloxy)ethyl)-3-piperidinecarboxylic acid;
or a pharmaceutically acceptable salt thereof.

19. A compound of claim 1 which is (R)-1-(2-(10,11-Dihydrodibenzo[b,f]oxepin-10-yloxy)ethyl)-3-piperidinecarboxylic acid; or a pharmaceutically acceptable salt thereof.

20. A pharmaceutical composition comprising a compound of claim 1 together with a pharmaceutical carrier or diluent.

21. The pharmaceutical composition of claim 20, in which said compound is present in said composition in an amount of 0.5 mg to 1000 mg per unit dose.

22. A method of treating a disorder in a subject in need of such treatment comprising administering to said subject an effective amount of a compound, wherein the disorder is selected from the group consisting of neurogenic inflammation, neuropathy, rheumatoid arthritis, migraine and itching and wherein the compound is a compound of formula I:

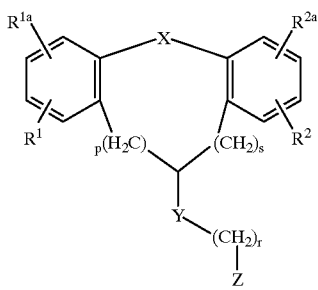

wherein
$R^1$, $R^{1a}$, $R^2$ and $R^{2a}$ independently are hydrogen, halogen, trifluoromethyl, hydroxy, $C_{1-6}$-alkyl, $C_{1-6}$-alkoxy or methylthio, —$NR^7R^8$ or -$SO_2NR^7R^8$ wherein $R^7$ and $R^8$ independently are hydrogen or $C_{1-6}$-alkyl;

X is —O— or —S—;

Y is —O—, —$S(O)_q$— wherein q is 0, 1 or 2, or —$N(R^5)$— wherein $R^5$ is hydrogen or $C_{1-6}$-alkyl;

s is 0 and p is 1 or s is 1 and p is 0;

r is 1, 2, 3 or 4;

Z is one of the following groups:

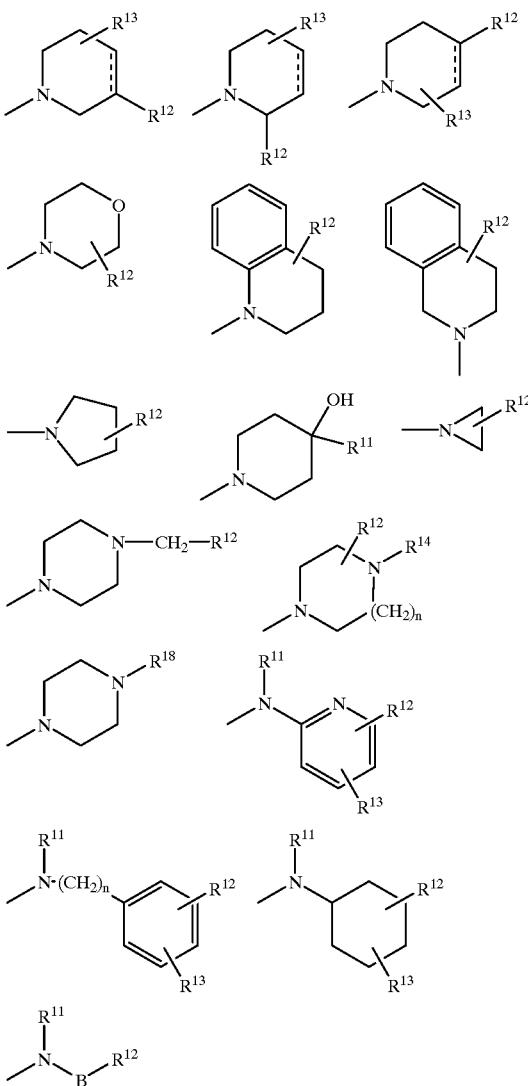

wherein n is 0, 1, or 2; $R^{11}$ is hydrogen, $C_{1-6}$-alkyl, $C_{1-6}$-alkoxy or phenyl optionally substituted with halogen, triflouromethyl, hydroxy, $C_{1-6}$-alkyl or $C_{1-6}$-alkoxy; $R^{12}$ is —$(CH_2)_mOH$ or —$(CH_2)_uCOR^{17}$ wherein m is 0, 1, 2, 3, 4, 5 or 6 and u is 0 or 1 and $R^{17}$ is —OH, —$NHR^{20}$ or $C_{1-6}$-alkoxy, wherein $R^{20}$ is hydrogen or $C_{1-6}$-alkyl; $R^{13}$ is hydrogen, halogen, trifluoromethyl, hydroxy, $C_{1-6}$-alkyl or $C_{1-6}$-alkoxy; $R^{14}$ is hydrogen or $C_{1-6}$-alkyl; B is $C_{1-6}$-alkylene, $C_{2-6}$-alkenylene or $C_{2-6}$-alkynylene; . . . is optionally a single bond or a double bond; and $R^{18}$ is one of the following groups:

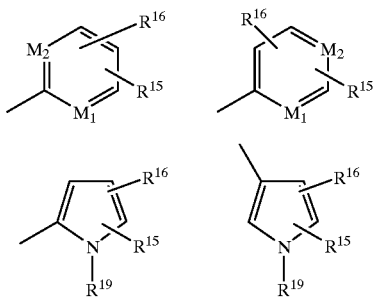

wherein $M_1$ and $M_2$ independently are C or N; $R^{19}$ is hydrogen, $C_{1-6}$-alkyl, phenyl or benzyl; $R^{15}$ is hydrogen, halogen, trifluoromethyl, nitro or cyano; and $R^{16}$ is hydrogen, halogen, trifluoromethyl, nitro, cyano, $-(CH_2)_m COR^{17}$, $-(CH_2)_m OH$ or $-(CH_2)_m SO_2R^{17}$, wherein m is 0, 1 or 2; or $R^{16}$ is one of the following groups:

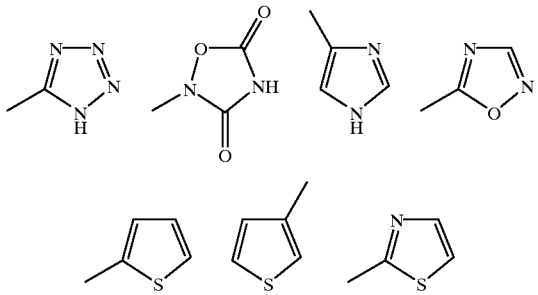

or a pharmaceutically acceptable salt thereof.

23. The method of claim 22, wherein the disorder is neurogenic inflammation.

24. The method of claim 22, wherein the disorder is neuropathy.

25. The method of claim 22, wherein the disorder is rheumatoid arthritis.

26. The method of claim 22, wherein the disorder is migraine.

27. The method of claim 22, wherein the disorder is itching.

28. A method for reducing blood glucose and/or inhibit the activity of CGRP in a subject in need of such treatment comprising administering to said subject an effective amount of compound wherein the compound is a compound of formula I:

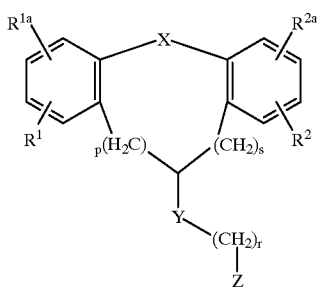

wherein $R^1, R^{1a}, R^2$ and $R^{2a}$ independently are hydrogen, halogen, trifluoromethyl, hydroxy, $C_{1-6}$-alkyl, $C_{1-6}$-alkoxy or methylthio, $-NR^7R^8$ or $-SO_2NR^7R^8$ wherein $R^7$ and $R^8$ independently are hydrogen or $C_{1-6}$-alkyl;

X is —O— or —S—;

Y is —O—, —S(O)$_q$— wherein q is 0, 1 or 2, or —N($R^5$)— wherein $R^5$ is hydrogen or $C_{1-6}$-alkyl;

s is 0 and p is 1 or s is 1 and p is 0;

r is 1, 2, 3 or 4;

Z is one of the following groups:

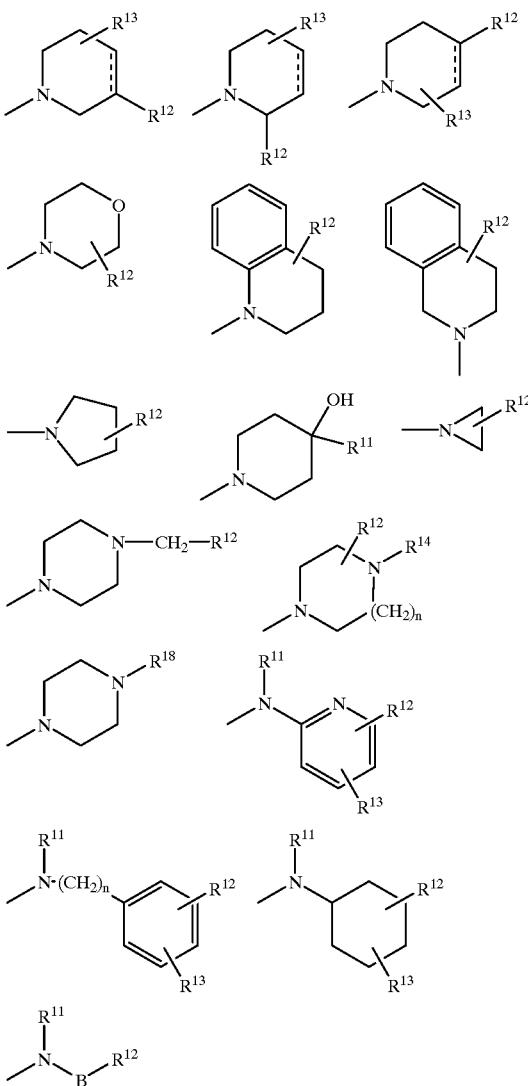

wherein n is 0, 1, or 2; $R^{11}$ is hydrogen, $C_{1-6}$-alkyl, $C_{1-6}$-alkoxy or phenyl optionally substituted with halogen, triflouromethyl, hydroxy, $C_{1-6}$-alkyl or $C_{1-6}$-alkoxy; $R^{12}$ is $-(CH_2)_m OH$ or $-(CH_2)_u COR^{17}$ wherein m is 0, 1, 2, 3, 4, 5 or 6 and u is 0 or 1 and $R^{17}$ is —OH, —NHR$^{20}$ or $C_{1-6}$-alkoxy, wherein $R^{20}$ is hydrogen or $C_{1-6}$-alkyl; $R^{13}$ is hydrogen, halogen, trifluoromethyl, hydroxy, $C_{1-6}$-alkyl or $C_{1-6}$-alkoxy; $R^{14}$ is hydrogen or $C_{1-6}$-alkyl; B is $C_{1-6}$-alkylene, $C_{2-6}$-alkenylene or $C_{2-6}$-alkynylene; . . . is optionally a single bond or a double bond; and $R^{18}$ is one of the following groups:

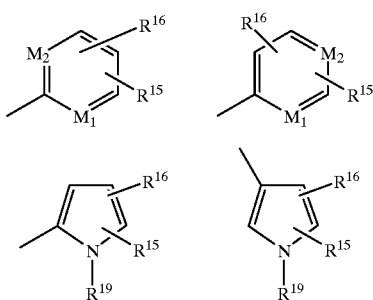

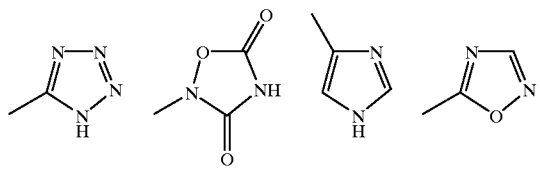

wherein $M_1$ and $M_2$ independently are C or N; $R^{19}$ is hydrogen, $C_{1-6}$-alkyl, phenyl or benzyl; $R^{15}$ is hydrogen, halogen, trifluoromethyl, nitro or cyano; and $R^{16}$ is hydrogen, halogen, trifluoromethyl, nitro, cyano, —$(CH_2)_m COR^{17}$, —$(CH_2)_m OH$ or —$(CH_2)_m SO_2 R^{17}$, wherein m is 0, 1 or 2; or $R^{16}$ is one of the following groups:

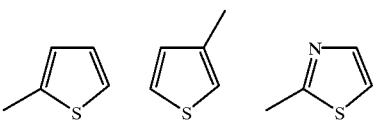

or a pharmaceutically acceptable salt thereof.

29. A compound which is (R)-1-(11H-Dibenz[b,f][1,4]oxathiepin-11-ylmethyl)-3-piperidinecarboxylic acid or a pharmaceutically acceptable salt thereof.

30. A pharmaceutical composition comprising a compound of claim 29 together with a pharmaceutical carrier or diluent.

31. The pharmaceutical composition of claim 30, in which said compound is present in said composition in an amount of 0.5 mg to 1000 mg per unit dose.

32. A method of treating a disorder in a subject in need of such treatment comprising administering to said subject an effective amount of the compound of claim 29, wherein the disorder is selected from the group consisting of neurogenic inflammation, neuropathy, rheumatoid arthritis, migraine and itching.

33. A method for reducing blood glucose and/or inhibit the activity of CGRP in a subject in need of such treatment comprising administering to said subject an effective amount of the compound of claim 29.

* * * * *